(12) United States Patent
Richards et al.

(10) Patent No.: US 11,819,202 B2
(45) Date of Patent: Nov. 21, 2023

(54) SYSTEMS AND METHODS INCLUDING AN ADJUSTABLE RETRACTOR FRAME

(71) Applicants: Robert Richards, Clawson, MI (US); Stephen Maguire, Shelton, CT (US)

(72) Inventors: Robert Richards, Clawson, MI (US); Stephen Maguire, Shelton, CT (US)

(73) Assignee: BIOPHYX SURGICAL, INC., Clawson, MI (US)

( * ) Notice: Subject to any disclaimer, the term of this patent is extended or adjusted under 35 U.S.C. 154(b) by 0 days.

(21) Appl. No.: 17/920,458

(22) PCT Filed: Oct. 25, 2021

(86) PCT No.: PCT/US2021/056510
§ 371 (c)(1),
(2) Date: Oct. 21, 2022

(87) PCT Pub. No.: WO2022/087537
PCT Pub. Date: Apr. 28, 2022

(65) Prior Publication Data
US 2023/0255611 A1 Aug. 17, 2023

Related U.S. Application Data

(60) Provisional application No. 63/134,782, filed on Jan. 7, 2021, provisional application No. 63/104,569, filed on Oct. 23, 2020.

(51) Int. Cl.
*A61B 17/02* (2006.01)
*A61B 17/00* (2006.01)

(52) U.S. Cl.
CPC .......... *A61B 17/0293* (2013.01); *A61B 2017/00946* (2013.01); *A61B 2017/00951* (2013.01); *A61B 2017/0287* (2013.01)

(58) Field of Classification Search
CPC ............ A61B 17/02; A61B 2017/0287; A61B 17/0293; A61B 46/00; A61B 46/20; A61B 2046/205; A61B 46/23
See application file for complete search history.

(56) References Cited

U.S. PATENT DOCUMENTS

| 2,845,925 A | 8/1958 | Jayle |
| 4,430,991 A | 2/1984 | Darnell |

(Continued)

FOREIGN PATENT DOCUMENTS

| EP | 2 873 376 | 5/2015 |
| GB | 2553313 | 3/2018 |
| WO | WO 2018/042159 | 3/2018 |

OTHER PUBLICATIONS

International Search Report snd Written Opinion PCT/US21/56510, dated Jan. 321, 2022.

*Primary Examiner* — Larry E Waggle, Jr.
(74) *Attorney, Agent, or Firm* — Neil D. Gershon

(57) ABSTRACT

The system includes a frame composed of materials and geometry allowing selective deformation in a plane perpendicular to a patient's anatomy at the surgical site but resisting deformation in a plane parallel to the anatomy. The frame is connected to stabilizing features and sheets, which are attached to adhesive to secure the frame to the patient. The features, sheets, and adhesive layers extend both into and beyond the frame. An integrated sheet covers the prospective incision site on the patient. When positioned at the site, the frame conforms to the patient. Anchor points are distributed along the frame to reversibly secure and provide a stable base for surgical retractors, even when unilaterally applied. By adaptable positioning and design of the stabilizing members and adhesive layers on the frame, the system is able to provide optimal tractional stability when experi- (Continued)

encing tensile loads in myriad surgical environments including ophthalmic and spinal surgery.

20 Claims, 16 Drawing Sheets

(56) References Cited

U.S. PATENT DOCUMENTS

| | | | |
|---|---|---|---|
| 4,434,791 | A | 3/1984 | Darnell |
| 4,643,181 | A | 2/1987 | Brown |
| 5,951,467 | A | 9/1999 | Picha et al. |
| 5,964,697 | A | 10/1999 | Fowler, Jr. |
| 6,190,311 | B1 | 2/2001 | Glines et al. |
| 6,572,541 | B1 | 6/2003 | Petersvik |
| 6,659,945 | B2 | 12/2003 | Ball et al. |
| 6,705,324 | B1 * | 3/2004 | Petersvik ........... A61B 17/0293 128/853 |
| 7,909,761 | B2 * | 3/2011 | Banchieri ............ A61B 1/0676 600/215 |
| 8,517,995 | B2 | 8/2013 | Voegele et al. |
| 8,857,440 | B2 | 10/2014 | Gundlapalli et al. |
| 2003/0055439 | A1 | 3/2003 | Koseki |
| 2004/0242969 | A1 | 12/2004 | Sherts et al. |
| 2005/0171404 | A1 | 8/2005 | Mische |
| 2007/0156023 | A1 | 7/2007 | Frasier et al. |
| 2007/0235038 | A1 * | 10/2007 | Alinsod ................. A61B 46/00 128/849 |
| 2018/0243039 | A1 | 8/2018 | Ramires et al. |

\* cited by examiner

SYSTEMS AND METHODS INCLUDING AN ADJUSTABLE RETRACTOR FRAME

CROSS REFERENCE TO RELATED APPLICATION(S)

This application claims the benefit of U.S. Provisional Application Nos. 63/104,569, filed Oct. 23, 2020, and 63/134,782, filed Jan. 7, 2021, which are incorporated by reference as if disclosed herein in their entireties.

BACKGROUND

Surgery is rapidly changing in response to the need to reduce healthcare costs while at the same time reducing risk of infection and spread of viruses that can compromise patient safety. Surgery utilizes multiple force vectors applied to various tissues to apply various forms of retraction to allow access to a surgical site. In the most basic scenario, these retractors are placed and held in position manually by surgeons and surgical assistants. This leads to compromised visualization of the operative site, compromised approach angles, and increased costs due to increased operating room staff and increased infection risk associated with additional personnel. Further, operator fatigue oftentimes leads to undesired placement or movement of retractors which requires revision by the surgeon leading to increased time under anesthesia and exposure and subsequently increased risk of adverse events. Furthermore, the requirement for intraoperative adjustments of anatomy presents challenges to the retraction techniques.

To mitigate the risks associated with human operators controlling retraction devices, there have been several attempts at non-manual retractor instruments that can minimize the number of personnel required in the operating room (reduced cost and risk). These devices include retractor frames and retractor components that engage with the tissue and attempt to provide retraction and adjustment of tissue by anchoring tissue to a relatively rigid frame that is placed around the operative site. However, it is common for such devices to compromise the surgical field visualization and access, require multiple hands for initial placement and readjustment of retractors, and commonly require repositioning during the procedure because they either inadvertently disengage from the site, or require repositioning, thereby complicating and prolonging the procedure. Mechanical holding arms that attach the retractor frame physically to the operating table aim to overcome some of these problems by preventing unintentional movement of the frame, but these add even more bulk and are difficult and time consuming to adjust if repositioning is required. Current retractor devices hinder the operation of surgical procedures which require the operated site be manipulated during the procedure. This is common, e.g., in shoulder surgery where the patient's arm is moved during the procedure. Further, repositioning of these traditional devices introduces opportunities for and risks of infection.

Additional attempts to solve these and similar problems include rigid metal retractor frames, typically anchored to the bed frame allow for attachment of various tools to assist with retraction. Protective membranes, e.g., Ioban™ or Tegaderm™ surgical drapes, have been used to reduce infection at the surgical site. Single use disposable plastic frames are typically anchored to the surgical site by the placement of multiple elastic "stays." The latter is mostly used to retract the superficial soft tissue and is not capable of substantial retraction forces. Further, these frames are not capable of unilateral retraction, i.e., require balanced retraction vectors to maintain frame position. Thus, should the retraction forces become unbalanced, retractors need to be repositioned. However, there remain limitations to retractor frames including the ability to accommodate intraoperative motion required during some procedures such as joint surgery that may require range of motion trialing. Additionally, retractor frames that are not affixed to the patient can be unstable.

The limitations of the current state of the retractor systems illustrates the need for a system suitable for anatomic repositioning mid-case.

SUMMARY

Aspects of the present disclosure are directed to a system for providing surgical retraction. In some embodiments, the system includes a frame composed of one or more flexible materials, the frame including a plurality of anchor points and at least one stabilizing member having one or more securing apparatus applied thereto to prevent motion of the system relative to a surgical site. In some embodiments, a securing apparatus is positioned outside of a perimeter of the frame and a securing apparatus is positioned inside of the perimeter of the frame. In some embodiments, the frame is composed of a biocompatible material including nylon, 304 annealed stainless steel, or combinations thereof. In some embodiments, one or more of the at least one stabilizing members includes one or more features positioned on, under, or in the one or more securing apparatus, or combinations thereof, the one or more features configured to provide tensile and compressive load resistance.

In some embodiments, at least one stabilizing member extends outwardly from the perimeter of the frame, inwardly from the perimeter of the frame, or combinations thereof. In some embodiments, one or more of the at least one stabilizing members includes a sheet integrated with the frame, one or more of the at least one stabilizing members, or combinations thereof. In some embodiments, the sheet includes one or more antimicrobial agents. In some embodiments, the sheet extends inwardly from the perimeter of the frame and is configured to be cuttable via a scalpel or open to a surgical application. In some embodiments, the securing apparatus includes an adhesive layer, a friction fit, gravity, suction, magnets, or combinations thereof.

Some embodiments of the present disclosure are directed to a system for providing surgical retraction including a frame composed of one or more flexible materials, the frame including a plurality of anchor points positioned around a perimeter thereof, and a plurality of stabilizing members extending from the frame, the stabilizing members including one or more adhesive layers to prevent motion of the system relative to a surgical site. In some embodiments, a stabilizing member extends outwardly from the perimeter of the frame and a stabilizing member extends inwardly from the perimeter of the frame. In some embodiments, the frame allows deformation in a plane substantially perpendicular to a surface of a patient's anatomy at the surgical site but resists deformation in a plane substantially parallel to the surface.

In some embodiments, the stabilizing members have a thickness gradient along an axis thereof. In some embodiments, the at least one stabilizing member includes a sheet extending outwardly from the perimeter of the frame, inwardly from the perimeter of the frame, or combinations thereof, and at least one feature extending outwardly from the perimeter of the frame, inwardly from the perimeter of the frame, or combinations thereof. In some embodiments, the sheet has a thickness between about 30 μm and about 100 μm and the at least one features have a thickness between about 100 μm, and about 0.5 cm. In some embodiments, the sheet extends inwardly from the perimeter of the frame to completely cover an interior space defined by the perimeter.

Some embodiments of the present disclosure are directed to a system for providing surgical retraction. In some embodiments, the system includes a frame including a perimeter, a first surface, and a second surface facing opposite the first surface. In some embodiments, the system includes a plurality of anchor points positioned around the perimeter. In some embodiments, the system includes at least one stabilizing member. In some embodiments, the system includes an adhesive layer applied to the second surface, the stabilizing members, or combinations thereof, the adhesive layer configured to reversibly adhere the system to a surface of a patient's anatomy.

In some embodiments, the at least one stabilizing member extends at least inwardly from the perimeter. In some embodiments, the adhesive layer extends outwardly from the perimeter of the frame and inwardly from the perimeter of the frame. In some embodiments, the frame allows deformation in a plane substantially perpendicular to a surface of a patient's anatomy at the surgical site but resists deformation in a plane substantially parallel to the surface.

In some embodiments, one or more of the at least one stabilizing members includes one or more features positioned on, under, or in the one or more adhesive layers, or combinations thereof, to prevent motion of the adhesive layer, the one or more features configured to provide tensile and compressive load resistance, the one or more features including elongated sections having a generally lattice-shaped construction. In some embodiments, the at least one stabilizing member includes a sheet extending outwardly from the perimeter of the frame, inwardly from the perimeter of the frame, or combinations thereof. In some embodiments, the sheet extends inwardly from the perimeter of the frame to completely cover an interior space defined by the perimeter. In some embodiments, the sheet includes one or more antimicrobial agents.

In some embodiments, the frame includes a plurality of interlocking segments including a plurality of end lock sections configured to reversibly engage with adjacent interlocking sections and a plurality of spline shafts inserted through engaged interlocking end lock sections of adjacent segments, the spline shafts having a first configuration permitting rotation of adjacent interlocking segments and a second configuration substantially preventing rotation of adjacent interlocking segments. In some embodiments, the system further comprises one or more turret bases disposed in a first surface of the segments and a plurality of frame augmentations configured to reversibly attach to the frame via at least one of the one or more turret bases. In some embodiments, the frame augmentations included one or more anchor points, turret towers, suture locks, suction guide turrets, powered illuminated components, or combinations thereof.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DESCRIPTION

Figure 1A:
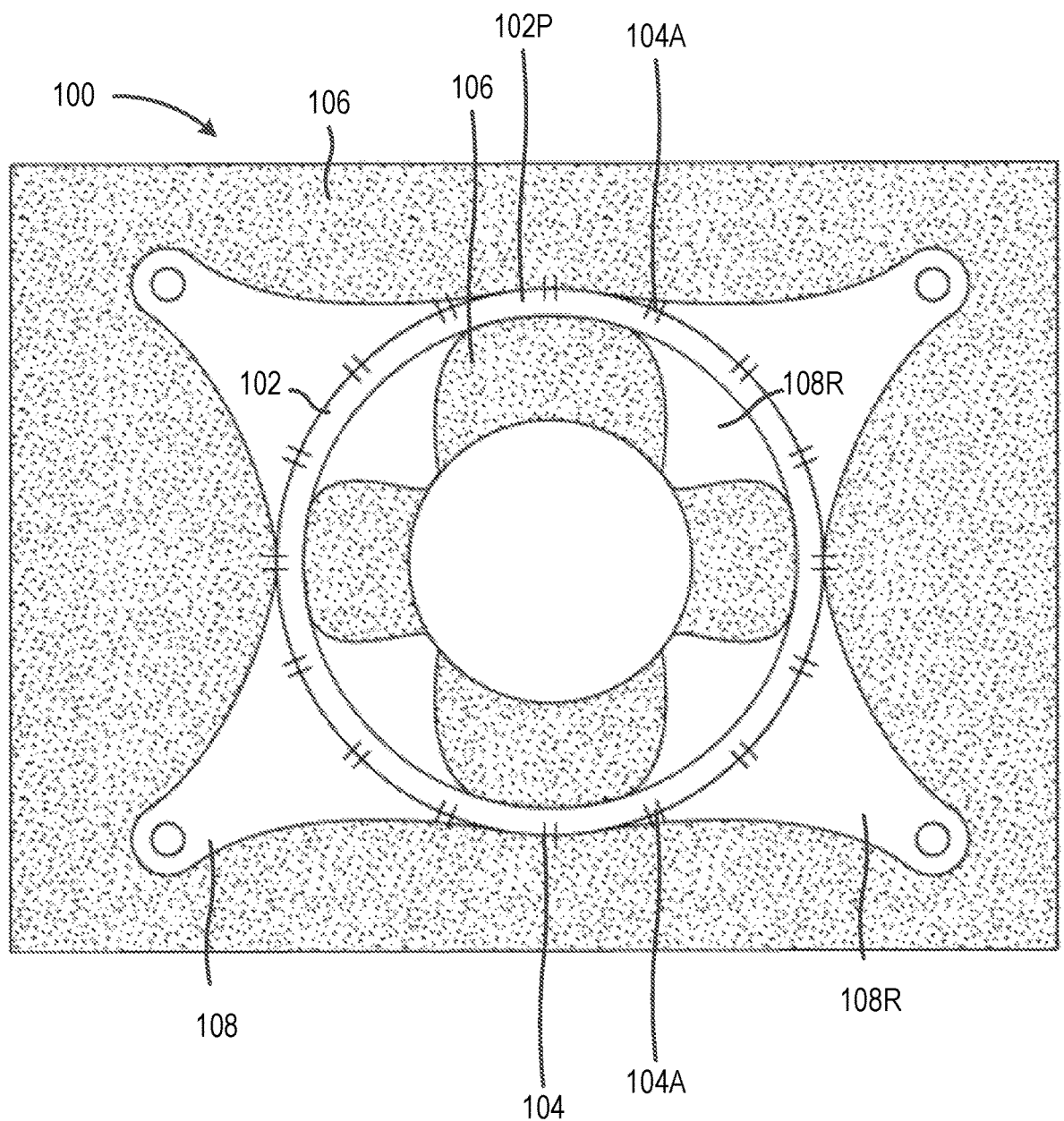
FIGS. 1A-1E are top and isometric view schematic drawings of a system for providing surgical retraction according to some embodiments of the present disclosure.
Figure 1B:
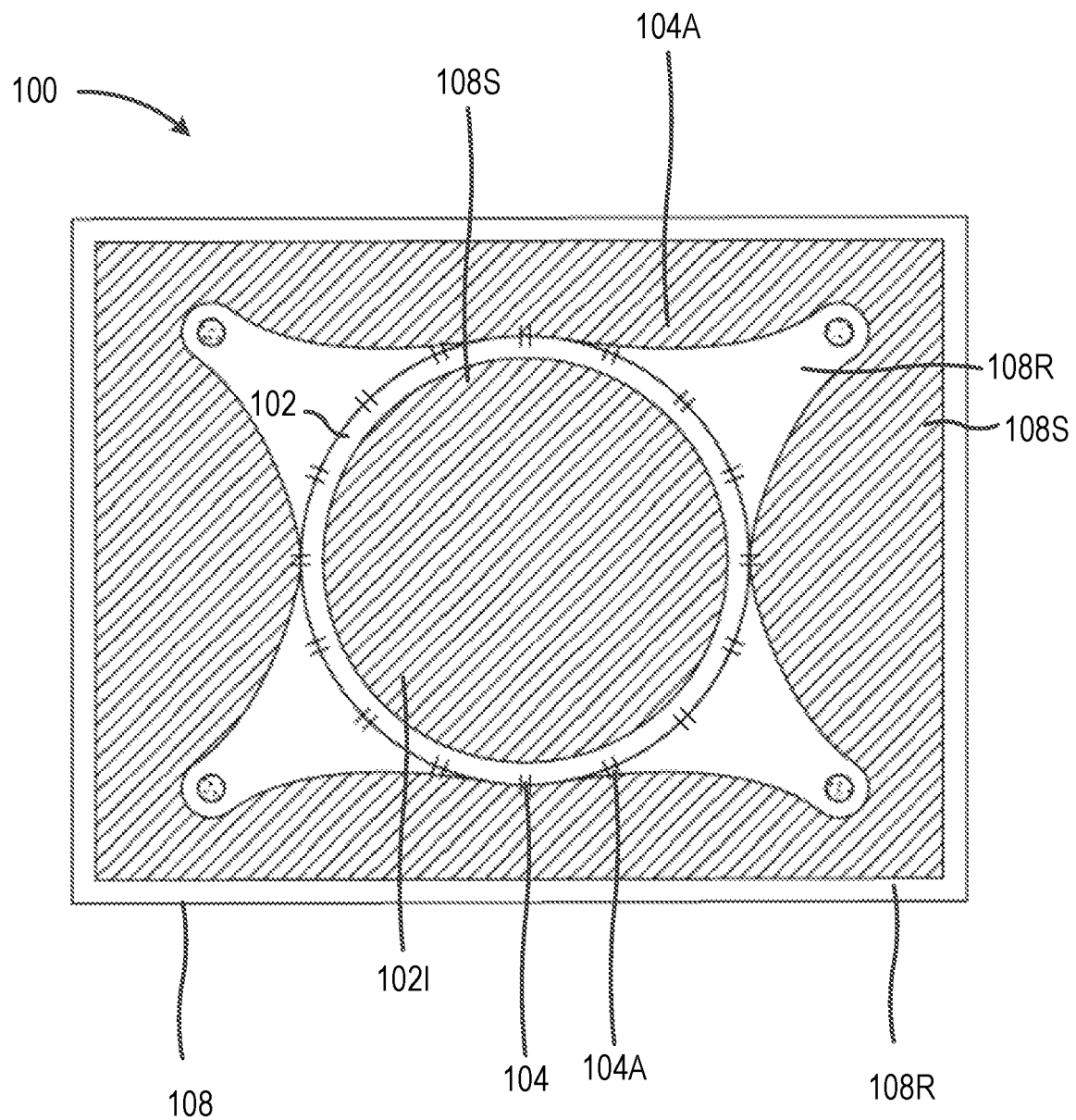
Figure 1C:
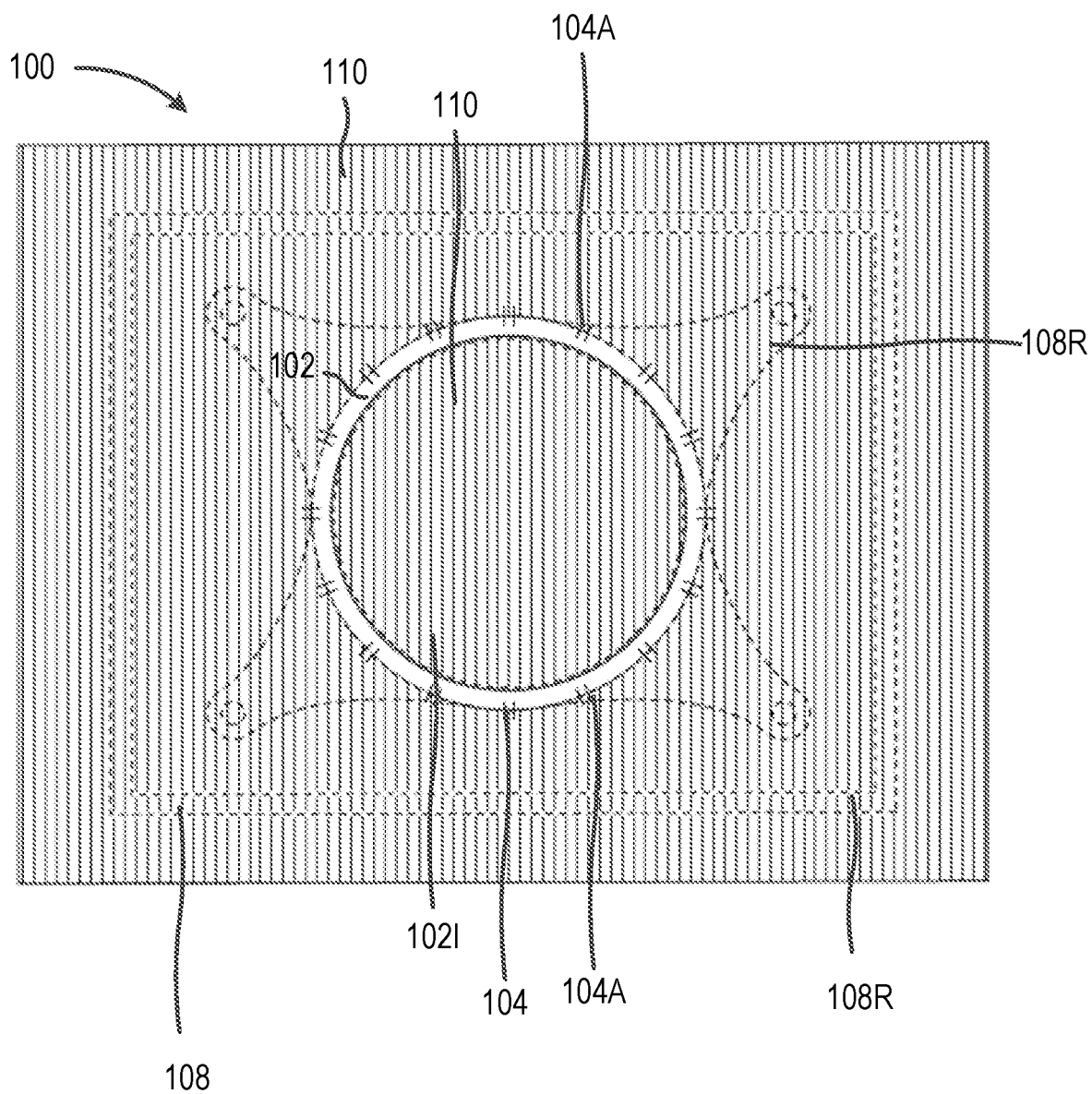
Figure 1D:
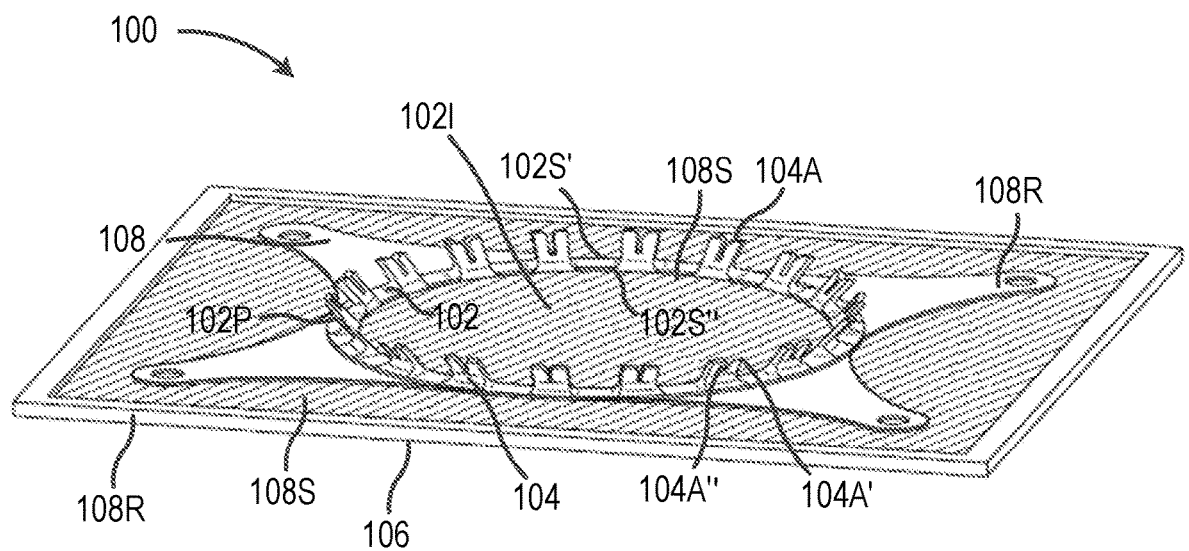
Figure 1E:
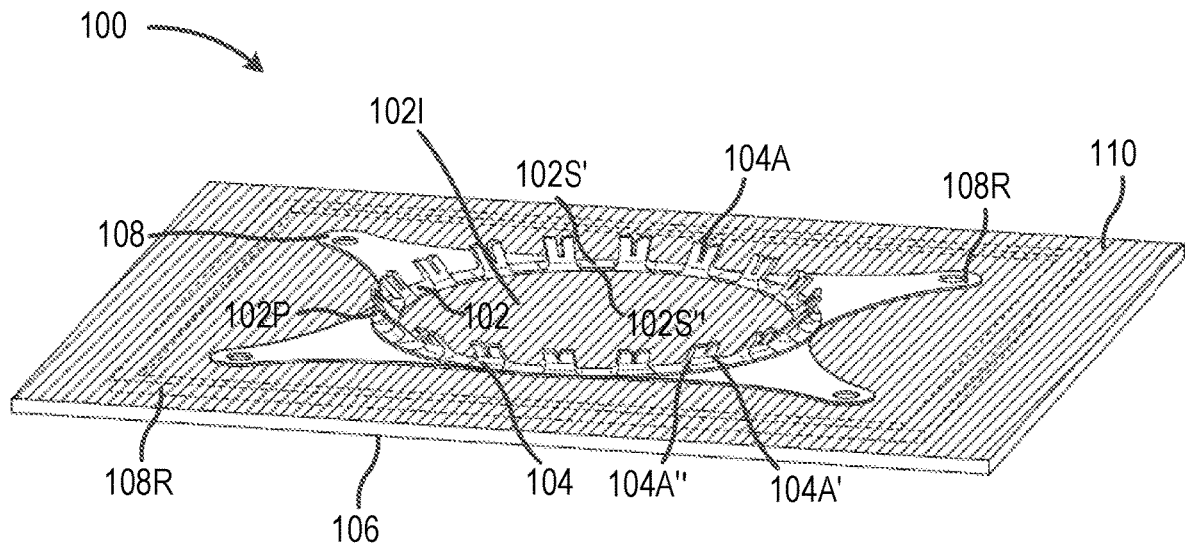

Referring now to FIGS. 1A-1E, some embodiments of the present disclosure are directed to a system 100 for providing retraction at a surgery site. In some embodiments, system 100 includes a frame 102. In some embodiments, frame 102 is configured to conform to a patient's specific anatomy, e.g., a surface of the patient's skin, surgical drapes, and the like, or combinations thereof. In some embodiments, frame 102 is configured to conform to the patient's anatomy, while also stabilizing one or more surgical tools during surgery, as will be discussed in greater detail below. In some embodiments, frame 102 is a ring, a segment thereof, ovular, a segment thereof, U-shaped, or combinations thereof. In some embodiments, frame 102 includes a perimeter 102P, a first surface 102S', and a second surface 102S". In some embodiments, second surface 102S" opposes first surface 102S', e.g., faces opposite the first surface. In some embodiments, perimeter 102P defines an interior space 102I, e.g., a circular frame defines the circular shaped space encircled by the frame, a U-shaped frame defines a space from the rounded base to the ends thereof, etc.

Frame 102 is of sufficient thickness and flexibility for use at a particular surgical site, e.g., more rigid for spinal surgeries and more flexible for neck surgeries. In some embodiments, frame 102 is composed of one or more flexible materials. In some embodiments, frame 102 is composed of one or more biocompatible materials. In some embodiments, frame 102 is composed of one or more biocompatible polymers, metals, or combinations thereof. In some embodiments, frame 102 is composed of nylon, 304 annealed stainless steel, or combinations thereof. In some embodiments, frame 102 includes at least one coating layer, e.g., a soft rubberized material for better comfort and integration with a sheet. In some embodiments, frame 102 allows deformation in a plane substantially perpendicular to a surface of a patient's anatomy at the surgical site but resists deformation in a plane substantially parallel to the surface, as will be discussed in greater detail below.

Still referring now to FIGS. 1A-1E, in some embodiments, frame 102 includes one or more anchor points 104. In some embodiments, frame 102 includes a plurality of anchor points 104. In some embodiments, anchor points 104 are positioned around perimeter 102P of frame 102. In some embodiments, frame 102 includes one or more elastic anchor points, one or more rigid anchor points, or combinations thereof. In some embodiments, frame 102 includes a plurality of elastic anchor points, rigid anchor points, or combinations thereof. Anchor points 104 enable the attachment of various tools, e.g., rigid retractor arms, elastic band retractors (such as the Lonestar Stays), other instrument attachments, or combinations thereof, while enabling a clear view during surgery. Anchor points 104 can be of any suitable shape so long as they are able to maintain the position of tools attached to frame 102 in a desired location, e.g., relative to a surgical site. In some embodiments, tools are maintained in position by a friction fit with one or more anchor points 104, mechanical locking, e.g., bayonet, interference fit, etc., or combinations thereof, as will be discussed in greater detail below. In some embodiments, anchor points 104 include one or more prongs 104A. In some embodiments, prongs 104A include at least a first finger 104A' and an adjacent second finger 104A". In some embodiments, prongs 104A, e.g., first finger 104A' and second finger 104A", extended from frame 102 in a direction non-parallel to the plane of the frame. In some embodiments, prongs 104A extended from frame 102 in a direction no more than 15 degrees from the surface of the patient's skin. In some embodiments, one or more tools are maintained in a desired position relative to a desired location via a friction fit between first finger 104A' and second finger 104A". In some embodiments, first finger 104A' and second finger 104A" extend distance from frame 102 to provide sufficient surface area between them to allow for a friction fit with a desired tool, e.g., an elastic band retractor.

Referring again to FIGS. 1A-1E, in some embodiments, system 100 includes one or more securing apparatus to secure system 100 in a desired position relative to a particular surgical site. In some embodiments, the securing apparatus secures system 100 directly to the patient. In some embodiments, securing apparatus secures system 100 to an intermediate layer, e.g., a surgical drape, which in turn is secured directly and/or indirectly to the patient. In some embodiments, the securing apparatus includes a friction fit, e.g., a rough surface that prevents movement of system 100 due to friction with the patient, a surgical drape, etc. In some embodiments, the securing apparatus utilizes gravity, e.g., system 100 is composed of sufficiently dense material that the weight of the system prevents movement relative to the patient, surgical drape, etc. when placed thereon. In some embodiments, the securing apparatus includes one or more magnets, e.g., system 100 magnetically attaches to magnets secured to the patient, a surgical drape, etc. In some embodiments, the securing apparatus includes one or more adhesive layers. In some embodiments, the securing apparatus includes suction, e.g., an applied vacuum holding system 100 to a patient. In some embodiments, system 100 includes one or more adhesive layers 106. Adhesive layer(s) 106 are configured and include sufficient adhesive to reversibly attach system 100 to a surface, e.g., a surface of the patient's skin, surgical drapes, and the like, or combinations thereof. In some embodiments, adhesive layer 106 is a continuous layer, semi-continuous layer, continuous coating, semi-continuous coating, or combinations thereof. In some embodiments, adhesive layer 106 is flexible to allow conformation to the contours of a patient's anatomy. In an exemplary embodiment, adhesive layer 106 is positioned and configured to reversibly immobilize frame 102 relative to an incision site for surgery, e.g., proximate the midline of the patient's neck, as will be discussed in greater detail below. In some embodiments, system 100 includes an adhesive layer 106 positioned outside perimeter 102P of frame 102. In some embodiments, system 100 includes an adhesive layer 106 positioned inside perimeter 102P of frame 102. In some embodiments, adhesive layer 106 is integrated with frame 102. In some embodiments, an adhesive layer 106 extends outwardly from frame 102. In some embodiments, an adhesive layer 106 extends inwardly from frame 102. In some embodiments, adhesive layer 106 is integrated with second surface 102S" of frame 102. In some embodiments, adhesive layer 106 includes one or more biocompatible adhesives. In some embodiments, adhesive layer 106 reversibly adheres to skin, e.g., of a human patient. In some embodiments, adhesive layer 106 maintains sufficient adhesion to allow for multiple uses, i.e., the frame is positioned and then can be repositioned at least once with system 102 still being useful for its intended purpose. In some embodiments, adhesive layer 106 includes a removable protective layer (not pictured). In some embodiments, the removable protective layer is configured to protect adhesive layer 106 until such time that it is desired for the adhesive layer to interface with a surface, e.g., a patient, surgical drapes, etc.

Referring again to FIG. 1A-1E, in some embodiments, system 100 includes at least one stabilizing member 108. In some embodiments, one or more of stabilizing members 108 are of sufficient thickness and/or suitable materials to resist bending. In some embodiments, one or more of stabilizing members 108 are flexible. In some embodiments, one or more of stabilizing members 108 are positioned outside perimeter 102P of frame 102. In some embodiments, one or more stabilizing members 108 are positioned inside perimeter 102P of frame 102. In some embodiments, one or more of stabilizing members 108 are positioned outside and inside perimeter 102P of frame 102. In some embodiments, one or more stabilizing members 108 are integrated with frame 102. In some embodiments, one or more stabilizing members 108 extend outwardly from frame 102. In some embodiments, one or more stabilizing members 108 extend inwardly from frame 102. In some embodiments, one or more stabilizing members 108 extend inwardly and outwardly from frame 102. In some embodiments, stabilizing members 108 are positioned proximate one or more boundaries of an adhesive layer 106. In some embodiments, stabilizing members 108 have a thickness between about 30 µm and about 0.5 cm. In some embodiments, stabilizing members 108 have a thickness between about 30 µm and about 1 mm. In some embodiments, stabilizing members 108 have a thickness between about 30 µm and about 100 µm. In some embodiments, the thickness of a stabilizing member 108 is variable along at least one axis thereof, as will be discussed in greater detail below.

In some embodiments, one or more of stabilizing members 108 include one or more features 108R. In some embodiments, feature 108R includes a body having a length and width. In some embodiments, feature 108R includes an elongated body having a width generally greater than a length, or vice-a-versa. In some embodiments, feature 108R includes one or more continuous surfaces. In some embodiments, feature 108R includes one or more stiffening features. In some embodiments, feature 108R includes one or more rib features that allow for bending along the axis of the rib but resist compressive and tensile forces. In some embodiments, feature 108R has a generally lattice-shaped construction. In some embodiments, feature 108R includes elongated sections having a generally lattice-shaped construction. In some embodiments, feature 108R has a thickness between about 100 μm and about 0.5 cm. The embodiment shown in FIG. 1A portrays a system 100 including 8 features 108R, however the present disclosure is not intended to be limited in this regard, as any number of stabilizing members 108 can be employed to help stabilize system 100 when positioned on a surface such as proximate an incision site, e.g., the exemplary embodiments in FIGS. 1B and 1C include 5 features 108R. In some embodiments, one or more features 108R are positioned outside perimeter 102P of frame 102. In some embodiments, one or more features 108R are positioned inside perimeter 102P of frame 102. In some embodiments, one or more features 108R are positioned outside and inside perimeter 102P of frame 102. In some embodiments, one or more features 108R are integrated with frame 102. In some embodiments, one or more features 108R extend outwardly from frame 102. In some embodiments, one or more features 108R extend inwardly from frame 102. In some embodiments, one or more features 108R extend inwardly and outwardly from frame 102.

In some embodiments, one or more stabilizing members 108 include one or more sheets 108S. Sheets 108S have a length and a width defining a surface area thereof, the sheet being flexible to conform to the corresponding surface area of a surface, e.g., proximate and/or covering an incision site on a patient. The embodiments shown in the figures portray a system 100 including generally rectangularly shaped sheets 108S, however the present disclosure is not intended to be limited in this regard, as any sheets 108S can be any suitable to help stabilize system 100 when positioned on a surface such as proximate an incision site and provide tensile and compressive load resistance, as will be discussed in greater detail below. In some embodiments, sheet 108S is formed of a suitable biocompatible material that is sufficiently flexible to conform to a patient's anatomy. In some embodiments, sheet 108S is formed from one or more polymers. In some embodiments, one or more sheets 108S are positioned outside perimeter 102P of frame 102. In some embodiments, one or more sheets 108S are positioned inside perimeter 102P of frame 102. In some embodiments, one or more sheets 108S are positioned outside and inside perimeter 102P of frame 102. In some embodiments, one or more sheets 108S cover the majority of an interior space 102I defined by perimeter 102P. In some embodiments, one or more sheets 108S cover the entirety of an interior space 102I defined by perimeter 102, e.g., is an incise drape. In some embodiments, one or more sheets 108S are integrated with frame 102. In some embodiments, one or more sheets 108S extend outwardly from frame 102. In some embodiments, one or more sheets 108S extend inwardly from frame 102. In some embodiments, one or more sheets 108S extend inwardly and outwardly from frame 102. In some embodiments, one or more sheets 108S include one or more antimicrobial agents. In some embodiments, one or more sheets 108S are configured to be cuttable via a surgical tool, e.g., where sheet 108S is an incise drape and is configured to cuttable with a scalpel.

In some embodiments, system 100 includes a single stabilizing member 108. In some embodiments, a single stabilizing member 108 is integrated with frame 102. In some embodiments, a single stabilizing member extends outwardly from frame 102 and inwardly from frame 102. In some embodiments, system 100 includes a single feature 108R. In some embodiments, system 100 includes a single sheet 108S. In some embodiments, system 100 includes a single feature 108R and a single sheet 108S. In some embodiments, system 100 includes a plurality of features 108R, a plurality of sheets 108S, or combinations thereof.

Figure 2A:
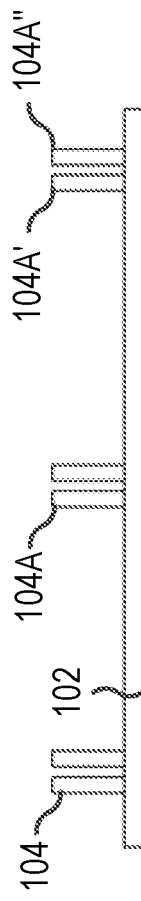
FIGS. 2A-2H are side view schematic drawings of a system for providing surgical retraction according to some embodiments of the present disclosure.
Figure 2B:
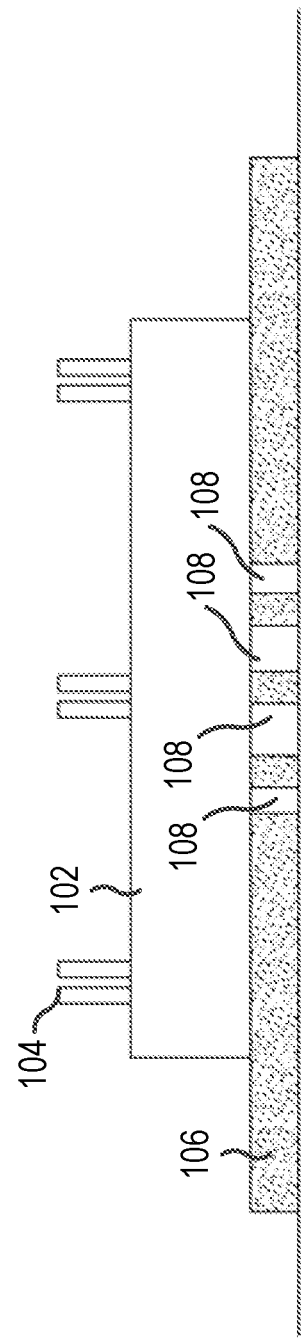
Figure 2C:
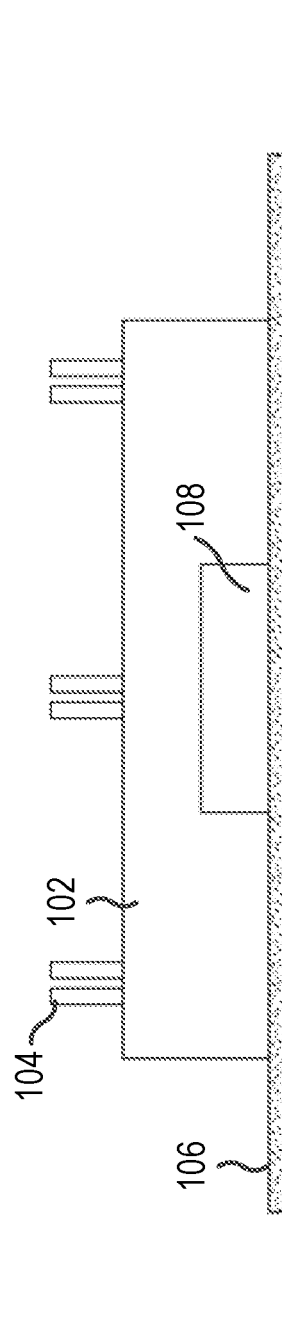
Figure 2D:
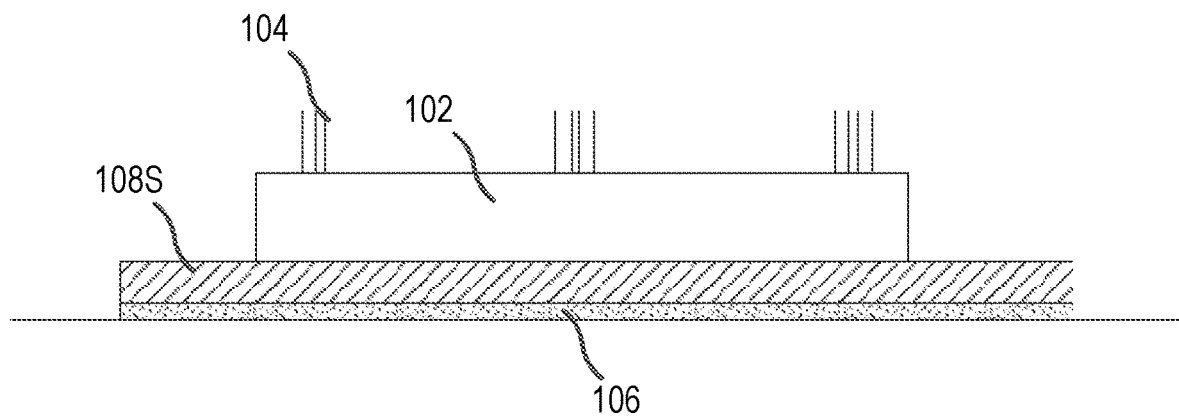
Figure 2E:
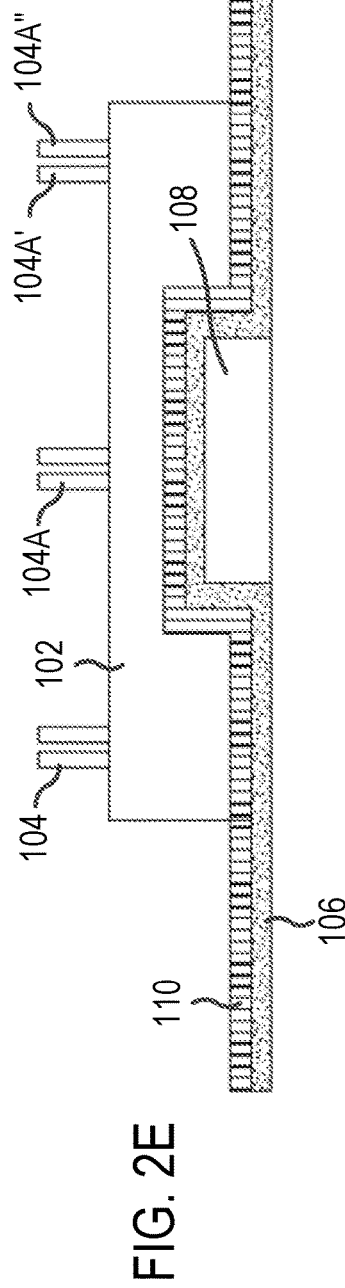
Figure 2F:
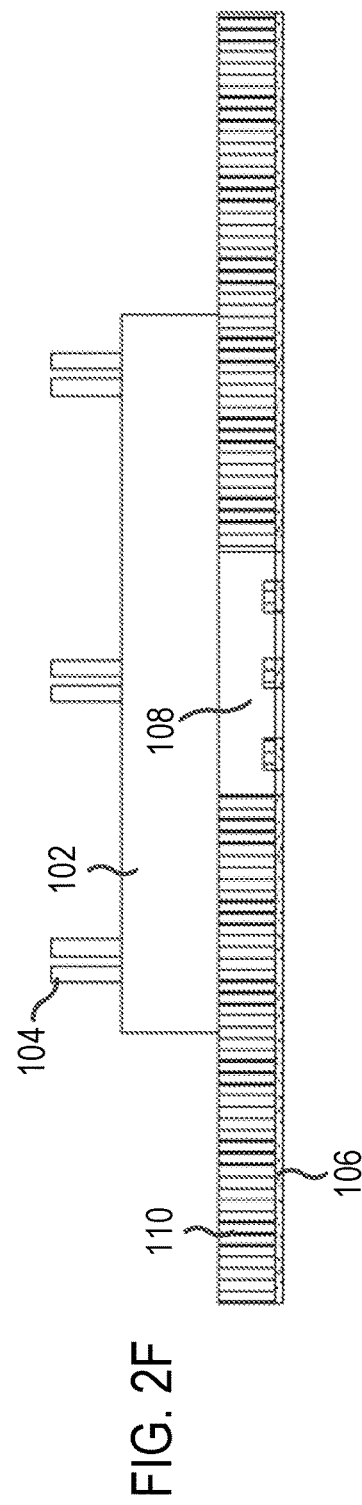
Figure 2G:
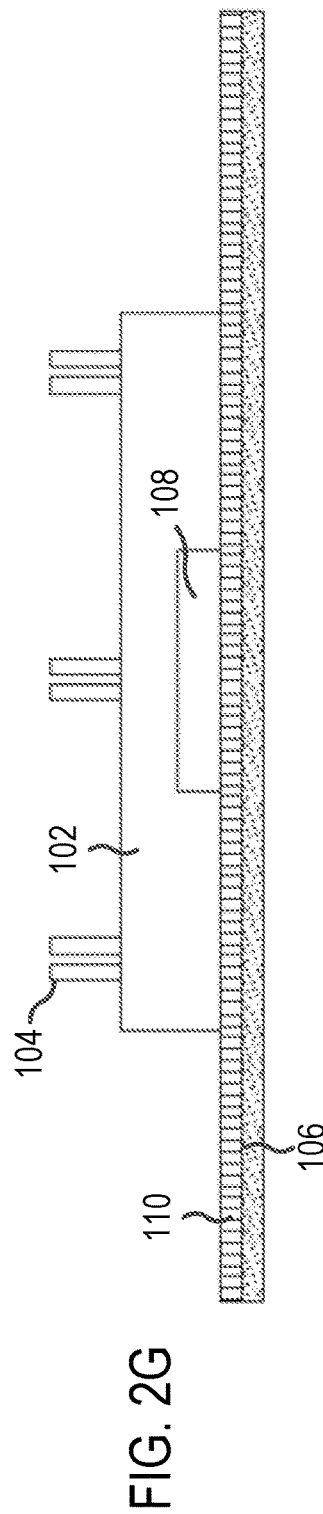

Referring now to FIGS. 2A-2H, in some embodiments, one or more stabilizing members 108 are integrated with an adhesive layer 106. In some embodiments, one or more stabilizing members 108 are positioned under an adhesive layer 106 (see FIG. 2A), in an adhesive layer 106 (see FIG. 2B), on an adhesive layer 106 (see FIG. 2C), or combinations thereof. In some embodiments, adhesive layer 106 covers an entire surface of a stabilizing member 108. In some embodiments, adhesive layer 106 covers only a portion of a stabilizing member 108. Referring specifically to FIG. 2D, in embodiments of system 100 with one or more sheets 108S, sheets are positioned on an adhesive layer 106. In some embodiments, system 100 includes one or more features 108R and one or more sheets 108S. In some embodiments, one or more features 108R are positioned on a sheet 108S, under a sheet 108S, or in a sheet 108S.

Figure 3:
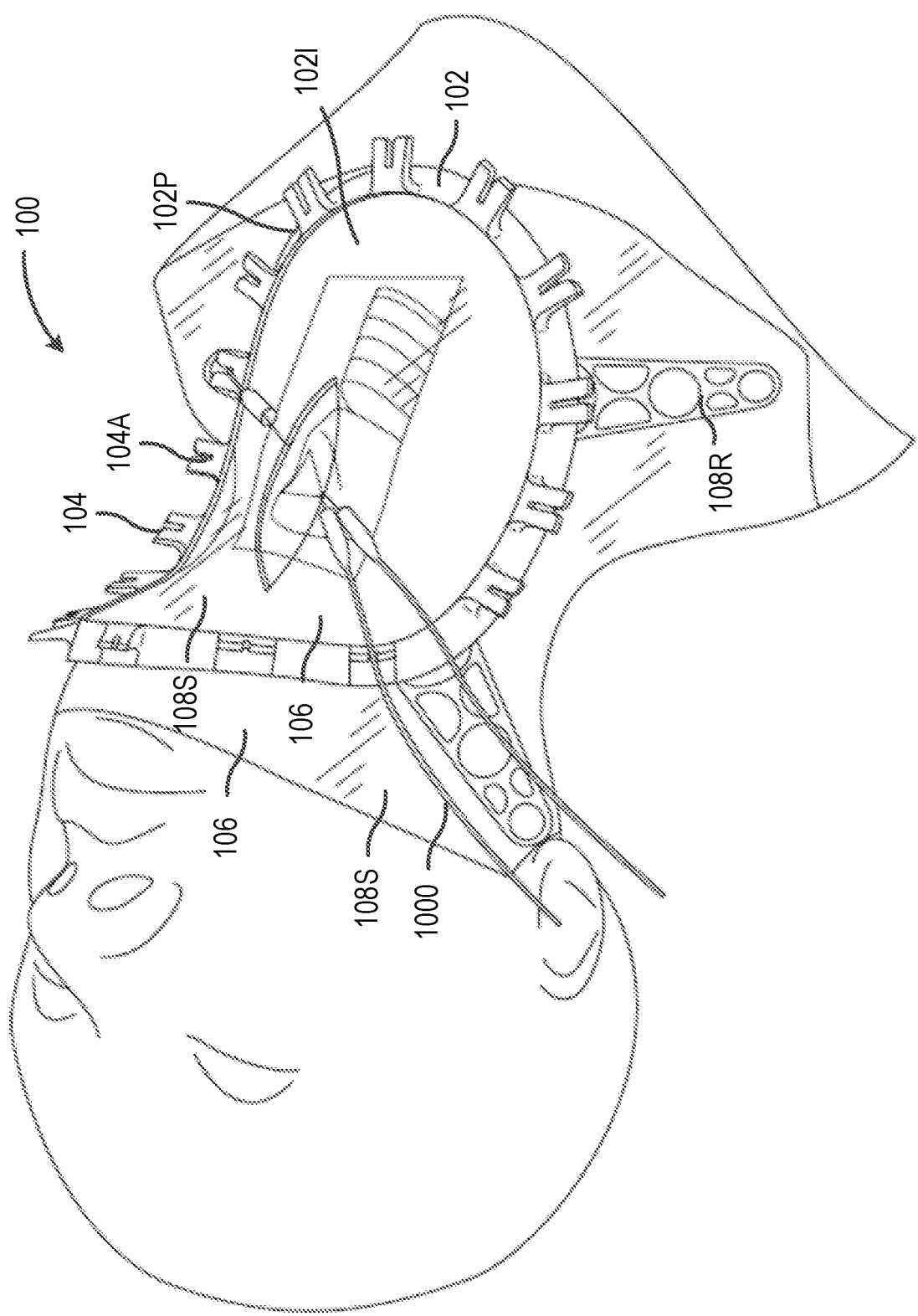
FIG. 3 is a schematic drawing of a system for providing surgical retraction according to some embodiments of the present disclosure in use on a patient.

Referring now to FIG. 3 showing embodiments of system 100 described above in use, the system is positioned on the patient's anatomy such that frame 102 is proximate an incision site. In some embodiments, system 100 is configured to resist and distribute tensile and compressive loads even while subjected to a bend radius of less than 45 mm. The embodiment shown in FIG. 3 portrays a system 100 in use for surgery on a patient's neck, however the present disclosure is not intended to be limited in this regard, as system 100 can be designed for use in a variety of surgical locations such as the neck (more flexible frame 102 and stabilizing members 108, bend radius between about 45 mm and about 125 mm), the spine (more rigid frame 102 and stabilizing members 108, bend radius greater than about 125 mm), the eye, (thinner frame 102 and/or stabilizing members, bend radius less than about 45 mm), etc.

In this exemplary embodiment, sheet 108S covers the area within perimeter 102P of frame 102, as well as an area surrounding perimeter 102P. Thus, when in use, the surgeon intuitively places an incision through sheet 108S, e.g., an incise drape, near the middle of frame 102. Rigid or elastic band retractors 1000 can then be attached to anchor points 104 on frame 102. Stabilizing members 108, i.e., features 108R and sheet 108S, integral with frame 102, act to hold system 100 in place.

As discussed above, frame 102 is configured to conform along an axis that is substantially parallel to the surface of the substrate, without allowing excessive flexion in an axis substantially perpendicular to the device. Adhesive layer 106 holds system 100 in place, affixing frame 102 and stabilizing members 108 such that the system sits relatively flush with the patient's anatomy. This allows for interoperative repositioning of the patient while maintaining strength sufficient to resist loads, e.g., from retractors 100. Further, system 100 distributes loads applied from attached devices/tools, e.g., retractors 1000, throughout frame 102 and stabilizing members 108 to the substrate to which the system is attached, i.e., patient's skin or surgical drape. Stabilizing members 108 are configured to provide tensile and compressive load resistance, distributing those loads over a larger area and reducing the loads felt by adhesive layers 106. This allows increased performance and ease of handling of adhesive layer 106, while also allowing the adhesive layer to conform to patient-specific anatomy. The coverage area of adhesive layers 106 and stabilizing members 108 contribute to the ability of system 100 to maintain position on the desired surface. As frame 102 is integrated with stabilizing members 108 which in turn have a large surface area, the loads applied are distributed over an expansive domain and this results in a very low risk of detachment or movement and, as a result, a high degree of security. By integrating a stabilizing member 108 with an adhesive layer 106 applied to the surface of patient's anatomy, motion of the adhesive layer is prevented, even on uneven surfaces with application of non-directional retraction forces applied to system 100. Sheet 108S may remain anchored to the surface of the operative site whilst allowing flexible frame 102 to deform when the patient's anatomy is repositioned without becoming detached from the operative site. Previous solutions would require repositioning with at least two hands, thereby extending length of surgery and complications.

Features 108R and sheets 108S also add resistance to the retractor holders that are anchored to frame 102. Without wishing to be bound by theory, due to stabilizing members 108 extending into and beyond perimeter 102P, forces applied to frame 102 by retractors 1000 affixed thereto are counteracted, thus stabilizing system 100 even when the forces applied by the retractors are otherwise unbalanced. The continuous frame 102 distributes these forces through a broader area of sheet 108S and/or features 108R, whereas a disconnected frame segment would have a much smaller area of sheet experiencing tensile loading. Through utilizing a large surface, compliant frame 102 can translate the loads placed by retractors 1000 from a single point on the device, throughout the frame and then distributed to other areas of sheet 108S that would not otherwise be loaded. This allows for much more efficient immobilization than if frame 102 was only stabilized by a smaller segment of sheet 108S or adhesive layer 106 just under the frame itself. The enlarged surface area of the attachment site increases the stability in the whole device so that retraction forces are easily balanced, even when retraction is mono-directional. In some embodiments, features 108R and sheet 108S are shaped in a way that anticipates retractor loading to maximize the amount of integral sheet that is intension.

Without wishing to be bound by theory, in some embodiments, control of loading forces to system 100 is performed via design and optimization of at least of the composition, thickness, and geometry of stabilizing members 108. By way of example, a highly flexible and/or very thin material, e.g., 30 μm thick polyurethane, would permit high bending and low compressive strength. Such a material would be preferable for use where loading would be minimal and patient anatomy would be complex, such as retraction of rectus muscles during ocular surgery. Substantially inflexible material, e.g., 0.5 cm polyetheretherketone, permits little if any bending, but maximizes compressive and tensile strength. Such a material would be preferable for use where loading is high but patient anatomy is relatively flat, e.g., retraction of paraspinal muscle elevation during a posterior laminectomy and system 100 is applied to the lower back with minimal curvature. More moderately flexible materials and/or material thicknesses, e.g., about 1 mm, therefore, permit some bending, but have higher compressive and tensile strength than the highly flexible/very thin material. Such a material would be preferable for applications with moderate loading and/or non-flat patient anatomy, e.g., retraction of soft tissue during anterior neck dissection as shown in FIG. 3. Further, as discussed above, in some embodiments, stabilizing members 108 can have a variable thickness, i.e., the thickness of the stabilizing members is not consistent throughout the member. For example, feature 108R might be thicker at a proximal end than at a distal end thereof, allowing for more compressive resistance at the proximal end (with less flexibility), but more flexibility at the distal end (with less compressive resistance when considering additive loading). Finally, in some embodiments, the geometry of stabilizing member 108 can be configured to more effectively distribute loading forces, e.g., by having a plurality of bending radii capabilities and associated compressive/tensile loading resistance capabilities. In some embodiments, stabilizing members 108 include a plurality of ribs that allow bending in the plane substantially perpendicular to frame 102 while still maintaining tensile compressive loading. In some embodiments, the geometry of stabilizing members 108 allows for more bending at the distal end thereof (where compressive and tensile loads are smaller) and less bending at the proximal end thereof (where compressive loads are higher due to the additive effect of the proximal portion of the stabilizing member).

In some embodiments, a protective layer is provided over adhesive layers 106 to protect the adhesive until it is time to position system 100. The protective layer is removed to allow exposure of adhesive layers 106. In some embodiments, adhesive layers 106 are exposed immediately prior to placement by the surgeon or surgical assistant and applied to the surface of contact. In some embodiments, system 100 further includes one or more straps (not pictured), that secure frame 102 to the patient e.g., around the neck, leg, back, etc., or another anchor point. In some embodiments, system 100 includes further includes one or more clamps (not pictured), e.g., clamping the frame to the patient, a bedframe, or other rigid structure.

Referring again to FIGS. 1C and 1E, in some embodiments, system 100 includes an surgical drape 110. In some embodiments, surgical drape 110 is integrated with frame 102, one or more of stabilizing members 108, or combinations thereof. Surgical drape 110 is configured to provide a barrier between surface upon which system 100 is applied, and a surrounding environment. In some embodiments, surgical drape 110 is positioned and configured to cover an incision site. In some embodiments, surgical drape 110 is configured to be cuttable via a surgical tool, e.g., a scalpel. In some embodiments, surgical drape 110 is positioned outside perimeter 102P of frame 102. In some embodiments, surgical drape 110 is positioned inside perimeter 102P of frame 102. In some embodiments, surgical drape 110 extends outwardly from frame 102. In some embodiments, surgical drape 110 extends inwardly from frame 102. In some embodiments, surgical drape 110 extends inwardly and outwardly from frame 102.

Figure 2H:
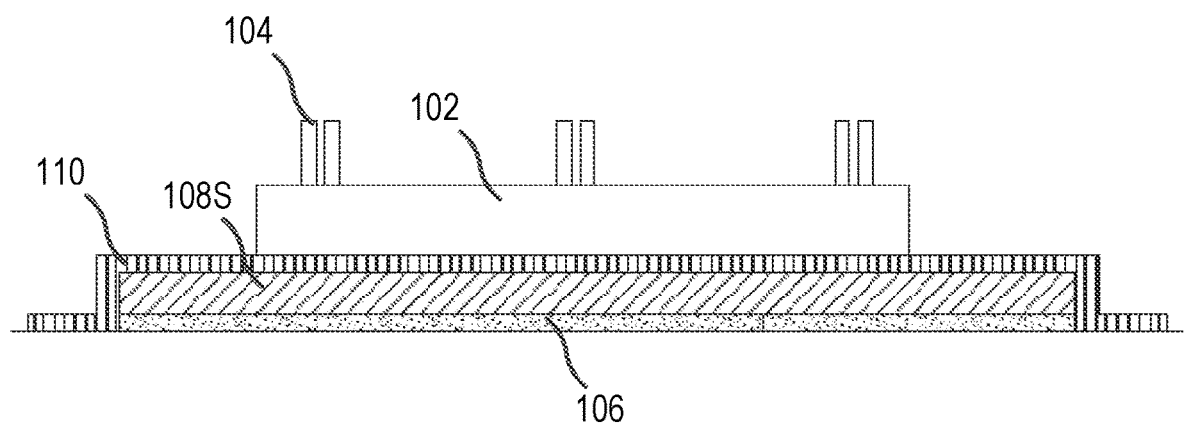

Referring again to FIGS. 2E-2H, in some embodiments, surgical drape 110 is integrated with an adhesive layer 106. In some embodiments, surgical drape 110 is positioned on stabilizing member 108 (see FIG. 2E), in stabilizing member 108 (see FIG. 2F), under stabilizing member 108 (see FIG. 2G), or combinations thereof. Referring specifically to FIG. 2H, in embodiments of system 100 with one or more sheets 108S, surgical drape 110 is integrated with a sheet 108S. In some embodiments, surgical drape 110 is coextensive with a stabilizing member 108. In some embodiments, surgical drape 110 has a larger surface area, i.e., a greater length, width, or combination thereof, than stabilizing members 108. In some embodiments, surgical drape 110 is attached to frame 102, stabilizing members 108, the patient, etc. via adhesive, magnets, hook and loop fasteners, or combinations thereof. In some embodiments, surgical drape 110 includes one or more antimicrobial agents.

Figure 8:
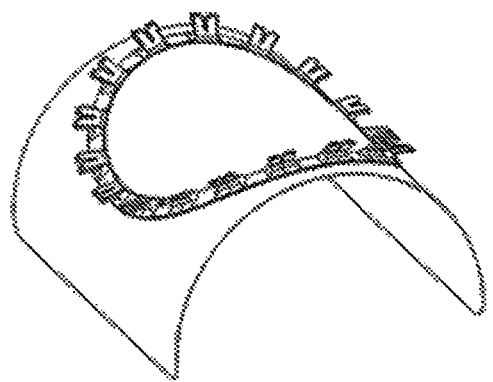
FIGS. 8 and 9 show a frame of the present invention conforming to a patient's anatomy and FIG. 10 shows a system of the present invention distributing loads applied from an attached device throughout the frame and membrane.
Figure 9:
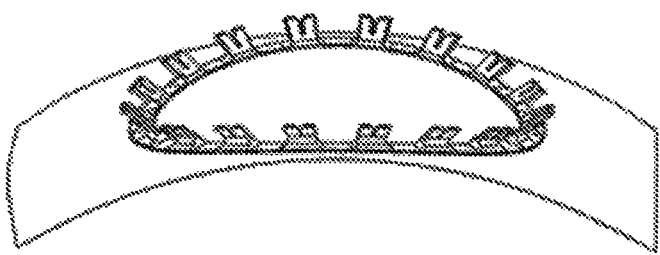
Figure 10:
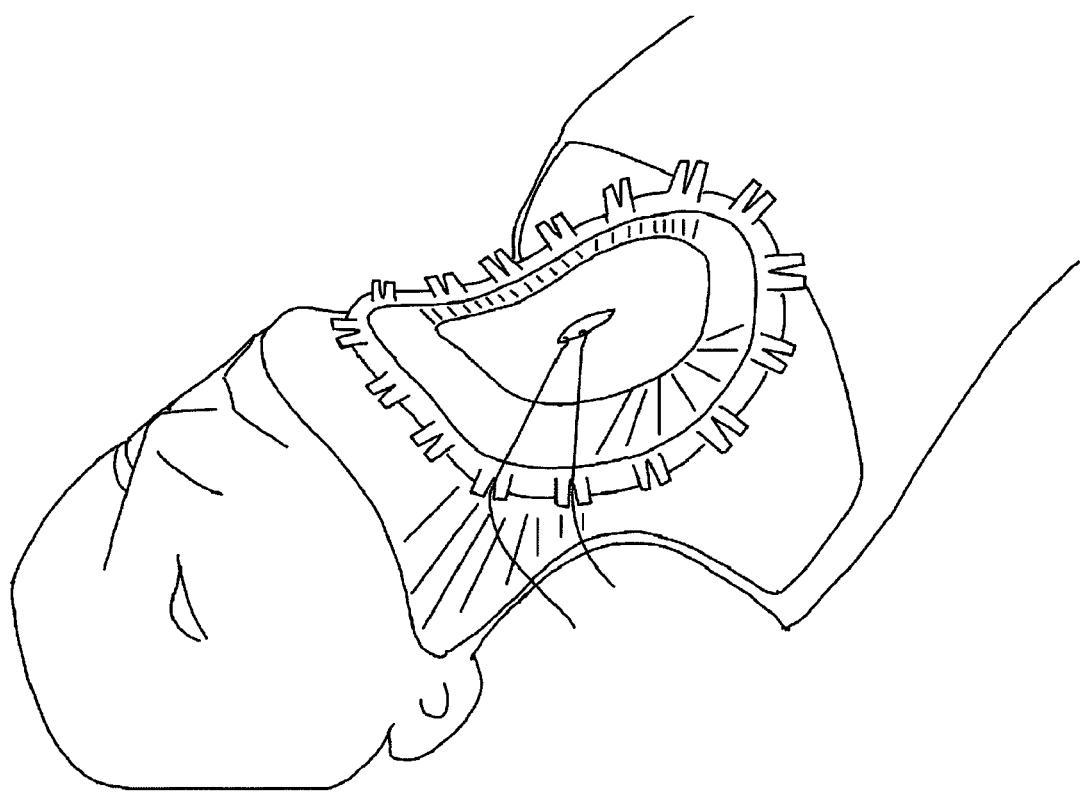

FIGS. 8-10 show an alternate embodiment of the present disclosure.

Referring now to FIGS. 8 and 9, in some embodiments, the frame is configured to conform to a patient's specific anatomy, e.g., a surface of the patient's skin, surgical drapes, and the like, or combinations thereof. In some embodiments, the frame is constructed out of one or more flexible materials, e.g., nylon. In some embodiments, the frame is constructed out of one or more malleable materials, e.g., 304 annealed stainless steel. In some embodiments, the frame is constructed out of at least one flexible material and at least one malleable material. In some embodiments, the frame includes at least one coating layer, e.g., a soft rubberized material for better comfort and integration with a membrane.

Referring now to FIG. 10, in some embodiments, the frame includes at least one anchor point. In some embodiments, the frame includes one or more elastic anchor points, one or more rigid anchor points, or combinations thereof. In some embodiments, the frame includes a plurality of elastic anchor points, rigid anchor points, or combinations thereof. These anchor points enable the attachment of various tools, e.g., rigid retractor arms, elastic band retractors (such as the Lonestar Stays), other instrument attachments, or combinations thereof, while enabling a clear view during surgery. The anchor points can be of any suitable shape so long as they are able to maintain the position of tools attached to the frame in a desired location, e.g., relative to a surgical site. In some embodiments, tools are maintained in position by a friction fit with one or more anchor points, mechanical locking, e.g., bayonet, etc., or combinations thereof. In some embodiments, the anchors include a plurality of prongs, between which tools can be held by frictional fit to maintain their position relative to the desired location.

Referring now to FIG. 8, in some embodiments, the frame is designed to conform to extreme patient anatomy. In some embodiments, the frame conforms to the patient's anatomy while providing sufficient stability for tissue retraction at the anchor points. In some embodiments, the frame is any suitable shape that allows deformation in the plane perpendicular to the surface of the anatomy but resists deformation in the plane parallel to the surface of the anatomy. In some embodiments, the frame is a ring, a segment thereof, ovular, a segment thereof, or combinations thereof.

As shown in FIG. 10, the system distributes loads applied from attached devices/tools throughout the frame and the membrane to the substrate the system is attached to, i.e., patient's skin or surgical drape. The image indicates a broad area of coverage provided by the protective membrane and the areas of membrane expected to be experiencing tensile loading, thereby reinforcing the position of the elastic retractors (areas of presumptive tensile loading with vector lines in black). As the frame is integral to the membrane which in turn has a large surface area, the loads applied are distributed over an expansive domain and this results in a very low risk of detachment or movement and, as a result, a high degree of security. The membrane may remain anchored to the surface of the operative site whilst allowing the flexible frame to deform when the patient's anatomy is repositioned without becoming detached from the operative site. Previous solutions would require repositioning with at least two hands, thereby extending length of surgery and complications.

The membrane also adds resistance to the retractor holders that are anchored to the frame. The image indicates the area of membrane that is resisting the loads of the elastic retractors. The continuous frame distributes these loads through a broader area of the protective membrane, whereas the disconnected frame segment has a much smaller area of protective membrane experiencing tensile loading (areas of presumptive tensile loading with vector lines in black). The displacement of the disconnected segment supports the finding that an integrated retractor membrane is substantially stronger. Through utilizing a large surface area as is available with membrane attachment, the compliant frame can translate the loads placed by retractors from a single point on the device, throughout the frame and then distributed to other areas of the integral membrane that would not otherwise be loaded, something not possible in a disconnected frame. This allows for much more efficient immobilization than if the frame was only stabilized by a smaller segment of integral membrane or just under the frame itself. The enlarged surface area of the attachment site increases the stability in the whole device so that retraction forces are easily balanced, even when retraction is mono-directional. In some embodiments, the integral membrane may be shaped in a way that anticipates retractor loading to maximize the amount of integral membrane that is in tension.

Figure 4:
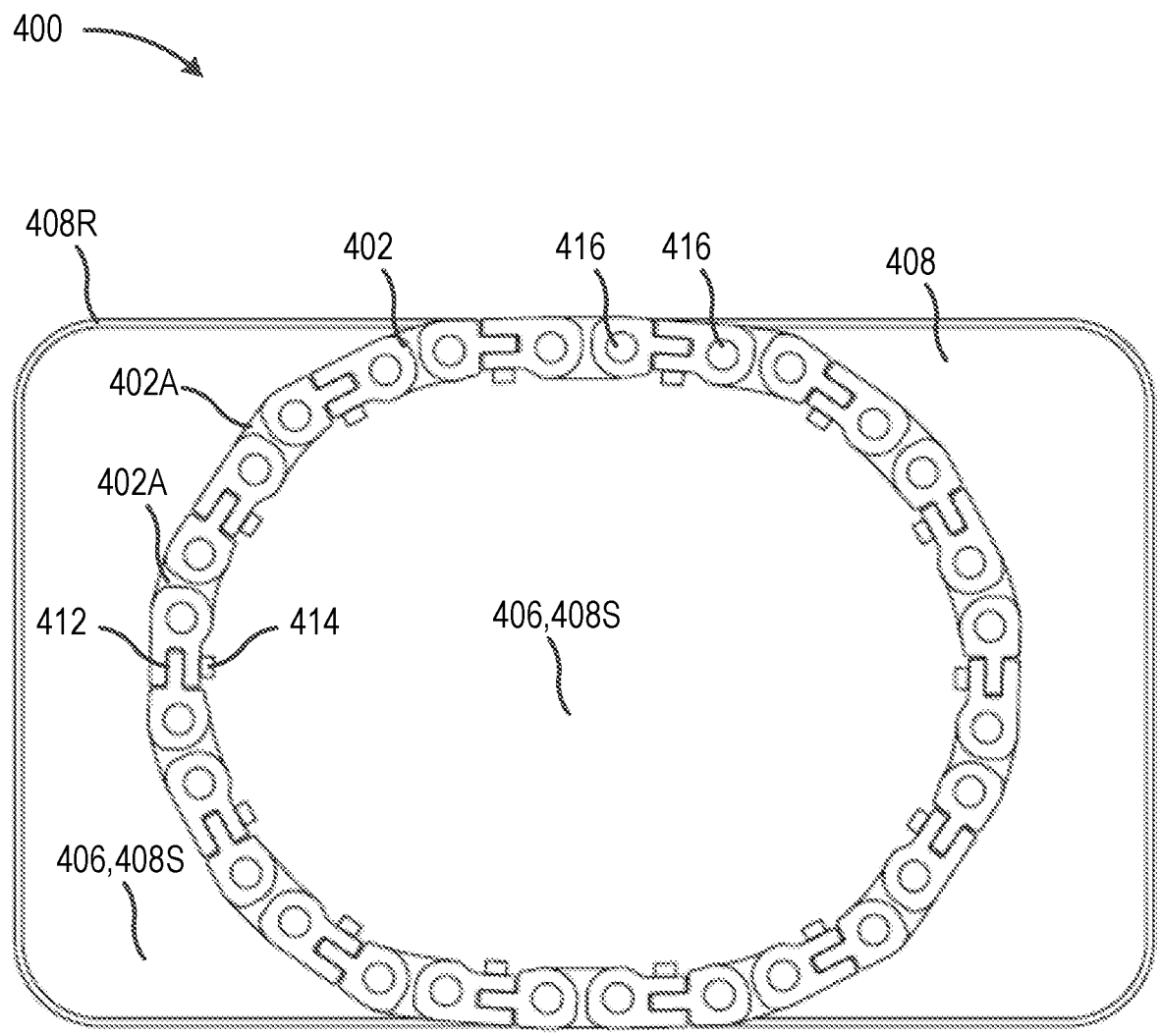
FIG. 4 is a top view schematic drawing of a system for providing surgical retraction according to some embodiments of the present disclosure.
Figure 6:
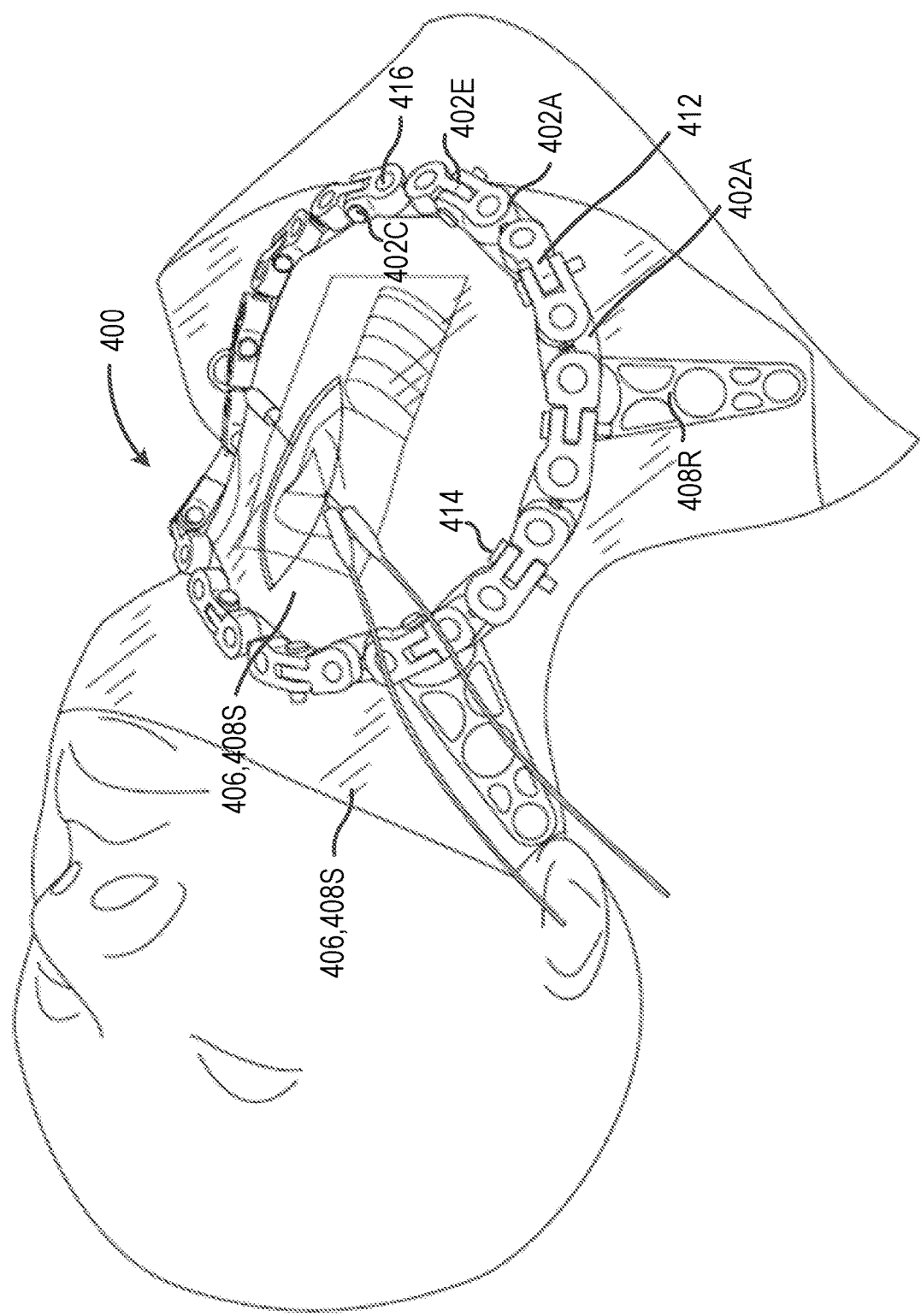
FIG. 6 is schematic drawings of a system for providing surgical retraction according to some embodiments of the present disclosure in use on a patient.

Referring now to FIGS. 4 and 6, some embodiments of the present disclosure are directed to a system 400 including a frame 402 including a plurality of interlocking segments 402A. In some embodiments, interlocking segments 402A are rigid, flexible, or combinations thereof. Other structural features of the embodiment of system 400 shown in FIG. 4, e.g., adhesive layers 406, stabilizing members 408 (such as feature 408R and sheet 408S), etc., can be substantially consistent with the embodiments discussed above with respect to FIGS. 1A-1E.

Figure 5A:
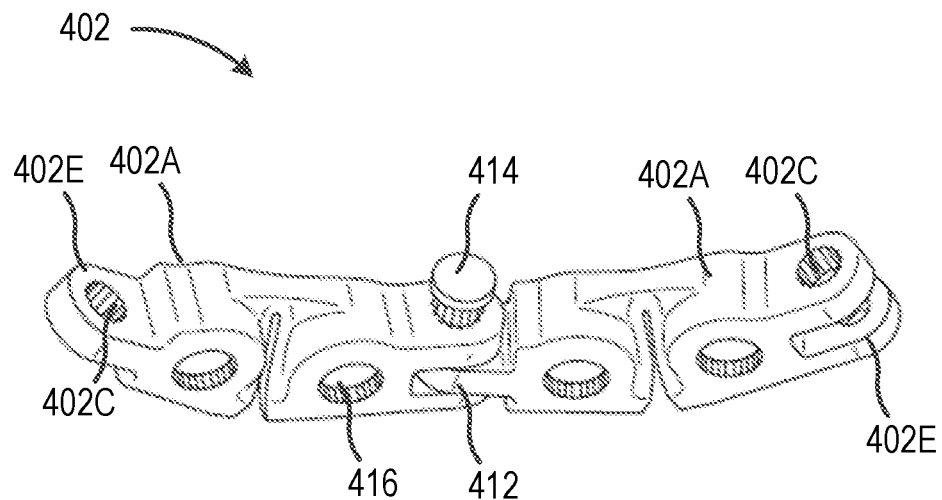
FIGS. 5A and 5B are schematic drawings of a frame including a plurality of interlocking segments according to some embodiments of the present disclosure.
Figure 5B:
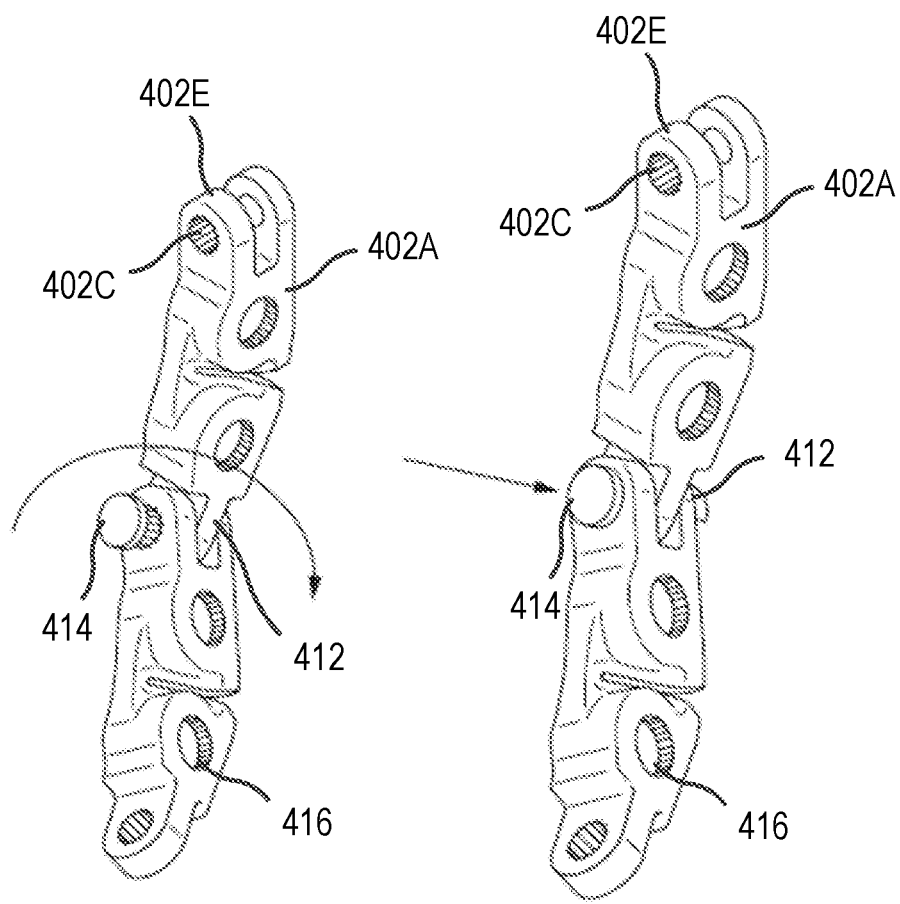

Referring specifically to FIGS. 5A-5B, in some embodiments, segments 402A include a plurality of end lock sections 402E configured to engage with adjacent sections 402E. In some embodiments, end lock sections 402E are configured to reversibly engage with adjacent sections 402E. End lock sections 402E connect adjacent interlocking segments 402A at a joint 412 that allows pivoting of the individual segments with respect to each other. In some embodiments, end lock sections 402E include one or more cavities 402C. Cavities 402C are positioned and configured to accept locking features 414 to hold adjacent interlocking segments 402A together and lock adjacent interlocking segments 402A at a desired orientation relative to each other. In some embodiments, locking features 414 reversibly hold adjacent interlocking segments 402A together and reversibly lock adjacent interlocking segments 402A at a desired orientation relative to each other. In some embodiments, frame 402 includes any suitable number of interlocking segments 402A. In some embodiments, frame 402 includes sufficient number of interlocking segments 402A to encircle a surgical site on a patient. In some embodiments, frame 402 includes 3 or more interlocking segments 402A, 4 or more interlocking segments 402A, 5, or more interlocking segments 402A, etc.

In some embodiments, locking features 414 can be any suitable mechanism for holding adjacent interlocking segments 402A together and locking adjacent interlocking segments 402A at a desired orientation relative to each other. In some embodiments, locking features 414 include spline shafts, expanding clamshells, revolver shafts, sliding wedges, or combinations thereof. In the exemplary embodiments shown in FIGS. 5A-5B and FIG. 6, a plurality of spline shafts are used as locking features 414. The spline shafts are inserted through aligned cavities 402C in engaged interlocking end lock sections 402E of adjacent interlocking sections 402A. As shown in FIG. 5B, the spline shafts have a first configuration that holds the adjacent interlocking sections 402A together, but permit them to rotate, and a second configuration that substantially prevents them from rotating.

Figure 7:
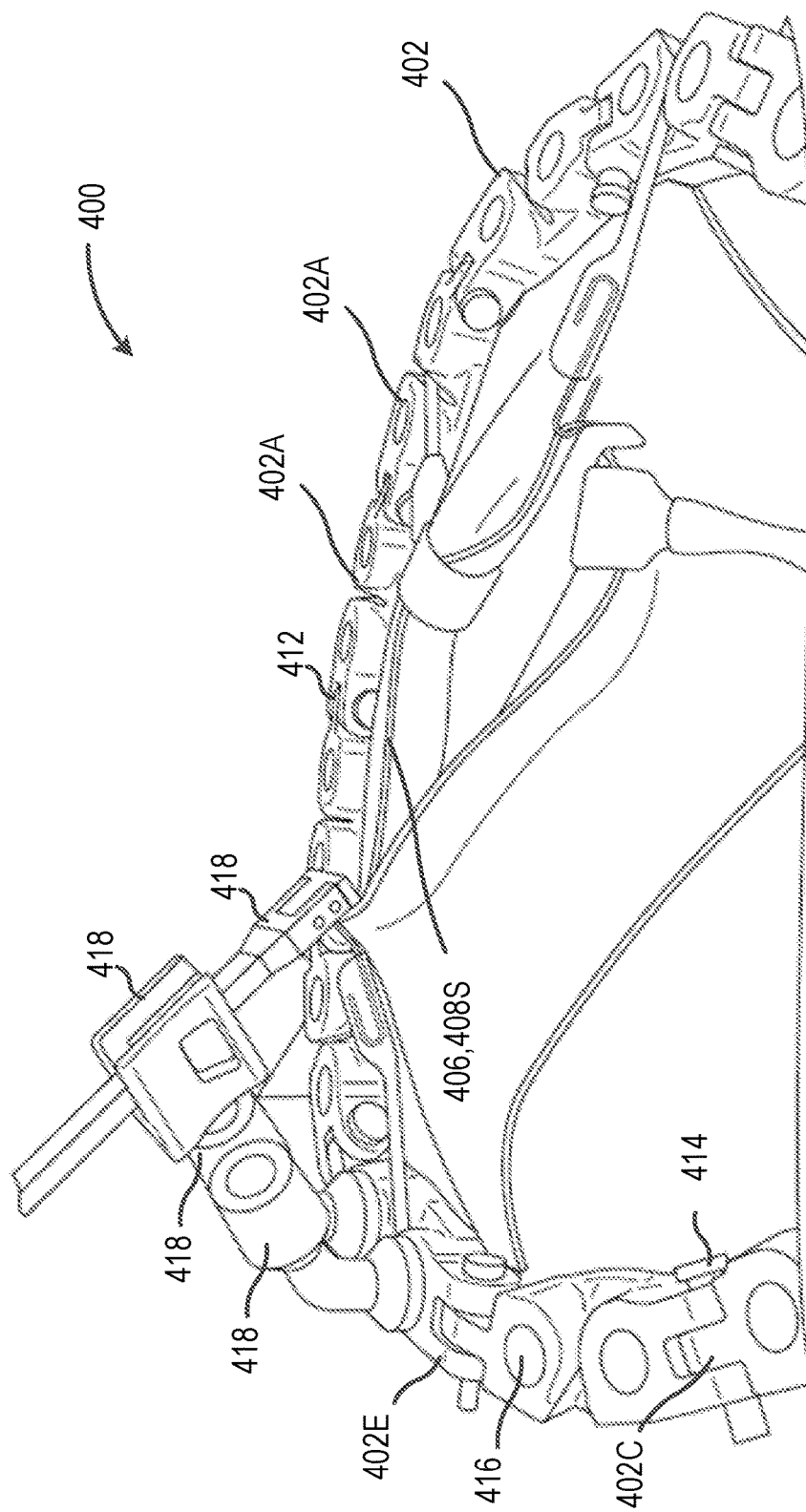
FIG. 7 is a schematic drawing of a system for providing surgical retraction including frame augmentations according to some embodiments of the present disclosure in use on a patient.

Referring again to FIGS. 4 and 5A-5B, interlocking segments 402A include one or more turret bases 416 disposed thereon, e.g., on a first surface. In some embodiments, turret bases 416 are configured to attach surgical tools to frame 402, e.g., via a friction fit, interference fit, mechanical lock, etc. In some embodiments, turret bases 416 are configured to releasably attach surgical tools to frame 402. An exemplary embodiment of system 400 is shown in FIG. 7 with a variety of frame augmentations 418, e.g., surgical tools, positioned on frame 402. In some embodiments, system 400 includes a plurality of frame augmentations 418. Frame augmentations 418 are configured to reversibly attach to frame 402 via a friction fit with at least one turret base 416. Exemplary embodiments of frame augmentations 418 include anchor points, turret towers, suture locks, suction guide turrets, powered illuminated components, or combinations thereof. The exemplary embodiment of FIG. 7 incorporates one or more turret towers and a retractor attached thereto. During various surgical procedures it is oftentimes desirable to retract from a vector that is not necessarily lateral to the surgical incision and to limit contact of the retractors on a patient's skin. To accomplish this, turret towers allow for tissue retraction from deep to superficial along a variety of paths depending on the height and angle of the tower. In some embodiments, various angulations are available to allow conformity to patient specific anatomy. In some embodiments, the lengths, angulations, or combinations thereof, of the turret towers are adjustable.

Thus, system 400 is composed of a frame 402 which conforms to a patient's specific anatomy, becomes rigid once conformation has been achieved, and maintains position and security throughout a surgical procedure, e.g., via an adhesive backing that adheres to the patient's skin and/or drapes. This exemplary embodiment allows joints 412 to rotate freely and once the desired position of the adjacent interlocking segments 402A is achieved, pushing in on locking features 414 makes the joint rigid, e.g. no longer flexible in the plane substantially perpendicular to frame 402. This allows for fast engagement of system 400 as well as minimizing the overall size and bulk of frame 402. Once all locking features 414 have been engaged, the collection of interlocking segments 402A results in a rigid frame which conforms to patient specific anatomy.

Methods and systems of the present disclosure are advantageous to provide an unobtrusive tissue retractor frame that is applied with stabilizing features and adhesive layers that can be securely fixed to a patient. The system attaches to a broad range of surfaces including skin and/or surgical drapes and provides rigid support for easily attachable tissue retractors and other implements, resists unintentional movement, and yet can move with the patient if clinically required by flexing the frame or unlocking segments of the frame. The conforming frame lays above the patient's skin and remains in position by utilizing the stabilizing members and adhesive layers. The frame also has sufficient rigidity to resist lateral movements applied by retractors. Since the frame in the systems of the present disclosure is conforming and adhering to the patient's skin, system stability is maintained without removal of the device even when subject to joint manipulation during the procedure. A surgeon thus has the confidence that once in position the system and surgical retractors can be expected to remain in position, and the surgeon's efforts and energy can remain consistently focused on the surgical procedure, rather than adjusting and/or resetting surgical retractors. The frame and the stabilizing members have a low profile, so as not impede visibility of an incision site and not obstruct movements of the surgeon and their tools during a procedure. The system is also highly versatile, capable of use in a variety of surgical environments, from ophthalmic to spinal surgery. This versatility also reduces costs for the surgeon, as a single system can be useful across multiple surgical environments and patient sizes.

The system can also include a modular, customizable, and reversibly assembled frame that provides greater visibility and multiple angles of approach while reducing the number of "hands" and clinicians to perform the surgery. The frames are assembled via quick and simple link locking and unlocking, providing an advantage over threaded methods. Attaching the frame directly to the skin/drapes also enables a low profile without sacrificing stability. The frames enable simultaneous, customizable, interchangeable mounting of multiple useful instruments, which is not only convenient but also results in fewer loose articles getting dropped or lost. By way of example, advantageous unilateral retraction at surgical sites, from deep to superficial retraction and allowing elastomeric stays to remain suspended above the patient's skin, e.g., by varying the height and angle of the retractor via one or more turret towers, is enabled.

Testing conducted indicates that a flexible protective sheet, positioned inside and outside the frame, provides maximal tractional stability when experiencing tensile loads, which can be optimized, e.g., by utilizing the combination of a frame and other stabilizing members that are more rigid than the sheet to translate forces throughout the system in order to maximize the available sheet that is in tension. Further, tensile and compressive loads are distributed over a broader surface, utilizing the patient's own anatomy as a support structure in a comprehensive stabilizing apparatus. Thus, otherwise inert areas of a patient have been repurposed to actively aid the surgeon at the incision site.

Finally, the systems of the present disclosure reduce the risk of infection throughout a surgical procedure. The frame, sheet/incise drape, and surgical drape can be provided as a unit and can be applied to the wound location at the same time, typically when the surgical area is being prepped. A system can thus cover the majority of, if not all, the surgical site prior to skin incision. The sheet/incise drape and surgical drape thus act as a physical barrier to prevent bacterial transmission and protecting of the surface of the skin from accidental nicks and cuts from surgical instrumentation. Further, the sheet/incise drape and surgical drape may include broad-spectrum antimicrobial properties that neutralize bacterial pathogens, enhancing protection of the sterile barrier in the event the sterile field is compromised.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A device for surgical retraction comprising:
   a frame having a lower surface, and an opposing upper surface and a periphery defining an interior space, the frame including at least one anchor point extending therefrom for retaining a tissue retraction member, the frame flexible to conform to a patient's anatomy; and
   a stabilizing member configured to provide tensile and compression load resistance, the frame integrated with the stabilizing member, the stabilizing member having a lower surface adhesively adhering to a skin of a patient or a surface overlying the skin of the patient to secure the frame and maintain position of the device relative to a surgical site, the stabilizing member extending underneath the frame, the stabilizing member and adhesive extending underneath an entire area of the frame, laterally outwardly from the periphery of the frame and laterally inwardly from the periphery of the frame toward an incision site into the interior space to thereby provide an adherence surface to an area larger than an area covered by the frame, the stabilizing member and underlying adhesive extending inwardly along an entire periphery of the frame.

2. The device of claim 1, further comprising a removable protective layer, the protective layer removable to expose the adhesive for securement of the stabilizing member to the skin or the surface overlying the skin.

3. The device of claim 1, wherein the frame is configured to allow deformation in a plane perpendicular to a surface of the patient's anatomy and resist deformation in a plane parallel to the surface of the patient's anatomy.

4. The device of claim 1, wherein the stabilizing member adds resistance to the tissue retraction member anchored to the at least one anchor point.

5. The device of claim 1, wherein the frame in a non-tensioned condition lies in a plane and has a first side and a second opposing side, the first and second sides bendable out of the first plane.

6. The device of claim 1, wherein the frame is non-circular in configuration.

7. The device of claim 1, wherein the stabilizing member comprises a membrane, and the frame is integrated with the membrane.

8. The device of claim 1, wherein the stabilizing member reversibly adheres to the skin or the surface and the adhesive providing the adhesive adherence maintains sufficient adhesion to allow for multiple uses of the frame for repositioning of the frame.

9. The device of claim 1, wherein the stabilizing member is configured to remain anchored to a surface of the patient's anatomy while the frame deforms to conform to the patient's anatomy when the patient's anatomy is repositioned without becoming detached from the skin or the surface overlying the skin.

10. The device of claim 1, wherein the stabilizing member counteracts forces applied to the frame by one or more tissue retraction members affixed to the at least one anchor point to thereby stabilize the device even when the retraction forces applied by the one or more tissue retraction members are unbalanced.

11. The device of claim 1, wherein the frame has sufficient rigidity to resist lateral movements applied by one or more tissue retraction members connected to the at least one anchor point.

12. The device of claim 1, wherein the stabilizing member comprises a membrane, and the frame is more rigid than the membrane to translate forces through the frame to maximize an area of the membrane that is in tension.

13. The device of claim 1, wherein the stabilizing member extends inwardly to completely cover the interior space defined by the periphery and cover a surgical site.

14. The system according to claim 1, wherein the stabilizing member comprises a membrane extending inwardly from the periphery of the frame and is configured to be cuttable via a scalpel.

15. The device of claim 1, wherein portions of the stabilizing member under tensile stress provide stability to the frame so that portions of the stabilizing member that are under compressive stress enable retraction from the frame.

16. The device of claim 1, wherein the at least one anchor point comprises a plurality of fingers spaced apart about the periphery and configured to frictionally maintain tissue retraction members secured to the fingers and the at least one anchor point extends laterally outwardly of an outermost edge of the frame and in a direction non-parallel to a plane of the frame.

17. A device for surgical retraction comprising:
a frame having a periphery, a lower surface and an opposing upper surface, the frame including at least one anchor point extending therefrom for retaining a tissue retraction member, the frame flexible to conform to a patient's anatomy; and
a stabilizing member attached to the frame, the frame integral with the stabilizing member and in contact with an upper surface of the stabilizing member along an entire bottom surface of the frame, the stabilizing member having a lower surface adhesively adhering to a skin of a patient or a surface overlying the skin of the patient to secure the frame;
wherein the frame integrated with the stabilizing member is configured to allow deformation in a plane perpendicular to a surface of the anatomy and resist deformation in a plane parallel to the surface of the anatomy wherein the stabilizing member remains anchored to the skin or surface while enabling the frame to deform when the patient's anatomy is repositioned.

18. The device of claim 17, wherein the stabilizing member is configured to remain anchored to a surface of the patient's anatomy while the frame deforms to conform to repositioning of the patient's anatomy.

19. A surgical retraction system for providing surgical retraction, comprising:
a frame having a periphery, a bottom surface, an opposing upper surface, and a periphery defining an interior surface, the frame including at least one anchor point extending therefrom for retaining a tissue retraction member, the frame flexible to conform to a patient's anatomy; and
a stabilizing member attached to the frame, the stabilizing member having a lower surface adhesively adhering to a skin of a patient or a surface overlying the skin of the patient to secure the frame, the stabilizing member extending inwardly along an entire periphery of the frame;
wherein the stabilizing member is configured to remain anchored to the surface of the anatomy while the frame deforms to conform to the patient's anatomy, wherein the system is configured such that the frame translates loads placed by a mono-directional retractor to the stabilizing member for distribution of the load.

20. The device of claim 19, wherein the frame in a non-tensioned condition lies in a plane and has a first side and a second opposing side, the first and second sides bendable out of the plane.

* * * * *